United States Patent
Saanum et al.

(10) Patent No.: US 9,688,614 B2
(45) Date of Patent: *Jun. 27, 2017

(54) ALTERNATIVE ACETYLATION PROCESS IN THE SYNTHESIS OF NON-IONIC X-RAY CONTRAST AGENTS

(71) Applicant: GE Healthcare AS, Oslo (NO)

(72) Inventors: Inger Dagny Saanum, Lindesnes (NO); Torfinn Haaland, Lindesnes (NO); Rita Heskestad Kalleberg, Lindesnes (NO)

(73) Assignee: GE Healthcare AS (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/100,683

(22) PCT Filed: Dec. 8, 2014

(86) PCT No.: PCT/EP2014/076885
§ 371 (c)(1),
(2) Date: Jun. 1, 2016

(87) PCT Pub. No.: WO2015/082719
PCT Pub. Date: Jun. 11, 2015

(65) Prior Publication Data
US 2016/0304438 A1 Oct. 20, 2016

Related U.S. Application Data

(60) Provisional application No. 61/969,932, filed on Mar. 25, 2014, provisional application No. 61/912,794, filed on Dec. 6, 2013.

(51) Int. Cl.
*C07C 231/02* (2006.01)
*C07C 237/46* (2006.01)

(52) U.S. Cl.
CPC ................ *C07C 231/02* (2013.01)

(58) Field of Classification Search
CPC ............ C07C 231/24; C07C 231/02
See application file for complete search history.

(56) References Cited

U.S. PATENT DOCUMENTS

| 4,250,113 A | 2/1981 | Holtermann et al. |
| 7,754,920 B1 | 7/2010 | Holmaas et al. |
| 7,863,484 B1 * | 1/2011 | Haaland ............... C07C 231/24 424/9.452 |

FOREIGN PATENT DOCUMENTS

| CN | 1132743 | * 10/1996 |
| EP | 2277851 A1 | 1/2011 |

OTHER PUBLICATIONS

International Search Report and Written Opinion regarding International Application No. PCT/EP2014/076885, mail date Jan. 29, 2015, 8 pages.

* cited by examiner

*Primary Examiner* — Jafar Parsa
*Assistant Examiner* — Amy C Bonaparte
(74) *Attorney, Agent, or Firm* — Wood IP LLC

(57) ABSTRACT

An alternative acetylation process for the synthesis of 5-acetamido-N,N'-bis(2,3-dihydroxypropyl)-2,4,6-triiodoisophthalamide ("Compound A"), an intermediate in the industrial preparation of non-ionic X-ray contrast agents, is described. The process can be performed on an industrial scale to produce Compound A with improved purity and improved yields compared to the established processes.

9 Claims, No Drawings

ALTERNATIVE ACETYLATION PROCESS IN THE SYNTHESIS OF NON-IONIC X-RAY CONTRAST AGENTS

CROSS-REFERENCE TO RELATED APPLICATIONS

This application is a filing under 35 U.S.C. 371 of international application number PCT/EP2014/076885, filed Dec. 8, 2014, which claims priority to U.S. application number 61/969,932, filed Mar. 25, 2014, and which claims priority to U.S. application number 61/912,794, filed Dec. 6, 2013, the entire disclosures of each of which are hereby incorporated by reference.

TECHNICAL FIELD

This invention relates generally to large-scale synthesis of non-ionic X-ray contrast agents. It further relates to an alternative acetylation process for the synthesis of 5-acetamido-N,N'-bis(2,3-dihydroxypropyl)-2,4,6-triiodo-isophthalamide ("Compound A"), an intermediate in the industrial preparation of non-ionic X-ray contrast agents. The process can be performed on an industrial scale to produce Compound A with improved purity and improved yields compared to the established processes.

BACKGROUND OF THE INVENTION

Non-ionic X-ray contrast agents constitute a very important class of pharmaceutical compounds produced in large quantities. 5-[N-(2,3-dihydroxypropyl)-acetamido]-N,N'-bis(2,3-dihydroxypropyl)-2,4,6-triiodo-isophthalamide ("iohexol"), 5-[N-(2-hydroxy-3-methoxypropyl)acetamido]-N,N'-bis(2,3-dihydroxypropyl)-2,4,6-triiodo-isophthalamide ("iopentol") and 1,3-bis(acetamido)-N,N'-bis[3,5-bis(2,3-dihydroxypropyl-aminocarbonyl)-2,4,6-triiodophenyl]-2-hydroxypropane ("iodixanol") are important examples of such compounds. They generally contain one or two triiodinated benzene rings.

For example, iodixanol, marketed under the trade name Visipaque®, is one of the most used agents in diagnostic X-ray procedures. It is produced in large quantities by GE Healthcare in Lindesnes, Norway. The industrial production of iodixanol involves a multistep chemical synthesis as shown in Scheme 1 below. See also U.S. Pat. No. 6,974,882. To reduce the cost of the final product, it is critical to optimize each synthetic step. Even a small improvement in reaction design can lead to significant savings in a large scale production.

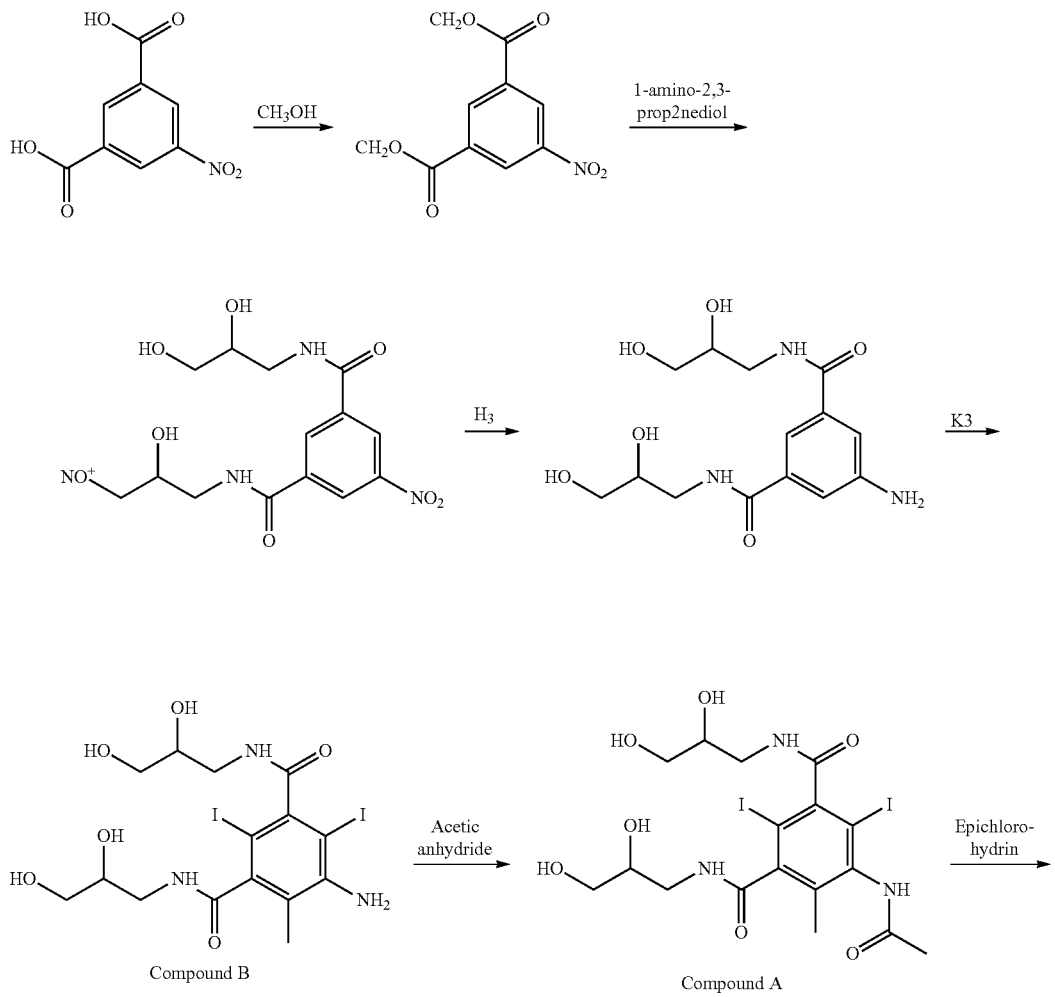

Scheme 1

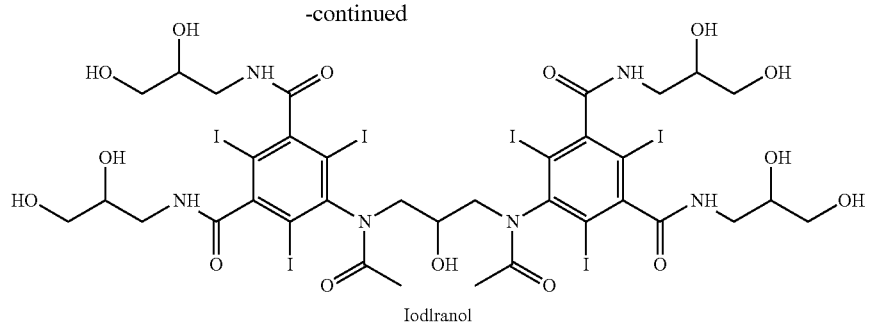

Iodlranol 5-acetamido-N,N'-bis(2,3-dihydroxypropyl)-2,4,6-tri-iodoisophthalamide ("Compound A") is a key intermediate in both the industrial scale synthesis of such non-ionic X-ray contrast agents. Compound A is prepared by the acetylation of 5-amino-N,N'-bis(2,3-dihydroxypropyl)-2,4,6-triiodo-isophthalamide (Compound B). The acetylation is achieved by using a mixture of acetic anhydride and acetic acid as the acetylating reagent. However, upon acetylation, not only is Compound A produced but several by-products are formed as well.

Thus there exists a need in the art for an acetylation process that can produce Compound A with a lower level of by-products; thus increasing both purity and yield of Compound A. Such an acetylation process must not only be able to be performed on a laboratory scale but also on an industrial scale. The instant invention, as described below, answers such a need.

SUMMARY OF THE INVENTION

According to the present invention, it has now been found that by significantly reducing the reaction temperature during the Compound B acetylation reaction, a reduction in the level of by-products produced can be achieved; hence higher yields and higher purity of Compound A can be produced. It has also now been found how to achieve such lower reaction temperature during the Compound B acetylation step on an industrial scale. Specifically, it has now been found that by adding a catalytic amount of an acid catalyst as described herein (e.g. para-toluene sulfonic acid (PTSA)) carefully into the Compound B acetylation reaction mixture over a period of several hours, lower acetylation temperatures can be achieved. In turn, the level of by-products formed in the acetylation is reduced which in turn results in improved purity of Compound A and consequently increased yield of Compound A in the subsequent purification steps. The present invention provides an alternative acetylation process for producing Compound A that can be performed on both a laboratory and/or industrial scale. In a preferred embodiment of the invention, the process is performed as a batch process. The present invention provides an alternative acetylation process for producing Compound A that can be performed as either a batch process or a continuous process. In a preferred embodiment of the invention, the process is performed as a batch process.

The present invention provides process comprising the steps of:

(i) reacting 5-amino-N,N'-bis(2,3-dihydroxypropyl)-2,4,6-triiodoisophthalamide ("Compound B") with a mixture of acetic anhydride/acetic acid to form a slurry;

(ii) heating said slurry to about 60° C.; and (iii) adding an acid catalyst (preferably, para-toluene sulfonic acid (PTSA)) to said slurry at a rate such that the reaction temperature is maintained at a temperature range of about 65-85° C.

The present invention also provides an industrial scale process comprising the steps of:

(i) reacting 5-amino-N,N'-bis(2,3-dihydroxypropyl)-2,4,6-triiodoisophthalamide ("Compound B") with a mixture of acetic anhydride/acetic acid to form a slurry;

(ii) heating said slurry to about 60° C.;

(iii) adding an acid catalyst (preferably, para-toluene sulfonic acid (PTSA)) to said slurry at a rate such that the reaction temperature is maintained at a temperature range of about 65-85° C. to form overacetylated Compound A; and (iv) deacetylating said overacetylated Compound A to form Compound A.

The present invention also provides an industrial scale process comprising the steps of:

(i) reacting 5-amino-N,N'-bis(2,3-dihydroxypropyl)-2,4,6-triiodoisophthalamide ("Compound B") with a mixture of acetic anhydride/acetic acid to form a slurry;

(ii) heating said slurry to about 60° C.; and (iii) adding an acid catalyst (preferably, para-toluene sulfonic acid (PTSA)) to said slurry at a rate such that the reaction temperature is maintained at a temperature range of about 65-85° C. to form overacetylated Compound A;

(iv) deacetylating overacetylated Compound A to form Compound A; and (v) isolating Compound A.

DETAILED DESCRIPTION OF THE INVENTION

In the established industrial scale process, Compound B is added to a mixture of acetic anhydride and acetic acid. The resulting slurry is then heated to approximately 60° C. When the temperature is achieved, an acid catalyst (e.g., para-toluene sulfonic acid (PTSA)(s)) is added in one portion and in catalytic amounts. Despite maximum cooling in the reactor jacket, the temperature of the reaction mixture increases rapidly to about 120-125° C. due to the exothermic acetylation reaction. The main part of the acetylation reaction will accordingly occur at 120-125° C. Because of the high reaction temperature, considerable levels of the following by-products I, II, and III in addition to Compound A are formed:

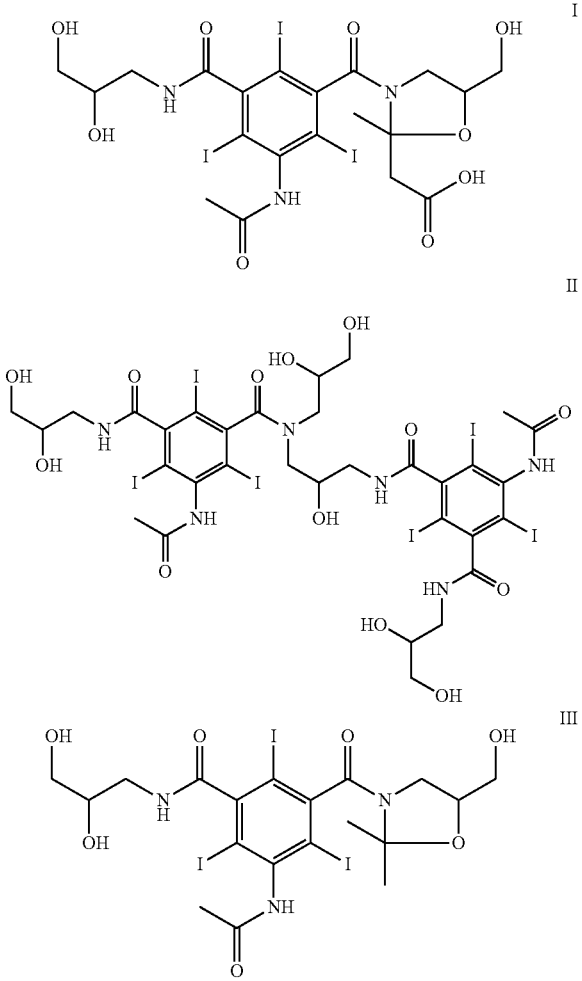

According to the present invention, an alternative acetylation process is provided. According to the present invention, Compound B is added to a mixture of acetic anhydride and acetic acid. The resulting slurry is then heated to approximately 60° C. At this temperature, a catalytic amount of an acid catalyst is added. Examples of a suitable acid catalyst include, for example, a sulfonic acid such as methanesulfonic acid, para-toluenesulfonic acid (PTSA) and sulphuric acid. Of these, para-toluenesulfonic acid (PTSA) is preferred. According to the invention, the acid catalyst can be added as a solid or as a solution. Examples of suitable solvents to form such a solution include acetic acid, acetic anhydride or a mixture of acetic acid and acetic anhydride. The addition is performed carefully while the temperature is controlled. In one embodiment, the PTSA is added as a solid in several portions. In one embodiment, the PTSA is added as a solution where PTSA is dissolved in a small volume of acetic acid. In one embodiment, the PTSA is added as a solution where PTSA is dissolved in a small volume of acetic anhydride. In one embodiment, the PTSA is added as a solution where PTSA is dissolved in a small volume of a mixture of acetic acid and acetic anhydride. The rate/speed of the addition of the acid catalyst, preferably PTSA, is such that the maximum reaction temperature is maintained at about 65-85° C. In general, the addition time will be over several hours in order to control the exothermic reaction.

In a preferred embodiment, the rate/speed of the addition of the acid catalyst, preferably PTSA, is such that the maximum reaction temperature is maintained at about 70-80° C.

According to the present invention, addition of the acid catalyst, preferably PTSA, produces a reaction mixture comprising overacetylated Compound A with lower levels of by-products compared to the established acetylation process. The reaction mixture comprising overacetylated Compound A can then be deacetylated using a deacetylating agent. There is no particular restriction upon the nature of the deacetylating agent used, and any deacetylating agent commonly used in conventional reactions may equally be used here. Examples of suitable deacylating agents include aqueous inorganic bases including alkali metal carbonates, such as sodium carbonate, potassium carbonate or lithium carbonate; and alkali metal hydroxides, such as sodium hydroxide, potassium hydroxide or lithium hydroxide. Of these, the alkali metal hydroxides, particularly sodium hydroxide or potassium hydroxide, and most preferably sodium hydroxide are preferred. For example, the reaction mixture comprising overacetylated Compound A can be deacetylated by the addition of base, such as sodium hydroxide, to form Compound A which in turn can then be purified (e.g., crystallization) and isolated by techniques known in the art.

The invention is illustrated further by the following examples that are not to be construed as limiting the invention in scope to the specific procedures described in them.

EXAMPLES

Examples 1 and 2 (Established Acetylation)

Acetylation: For both Examples 1 and 2, Compound B (200 g) was added to a mixture of acetic anhydride (191.8 mL) and acetic acid (103.3 mL). The slurry was heated to approximately 60° C., before PTSA powder (1.0 g) was added in one portion. Because of the exothermic reaction, the temperature rapidly increased to approximately 120-125° C.

In Example 1, the temperature were held at about 120° C. for approximately 2 hours to form over-acetylated Compound A, before moving on to the next deacetylation process step to form Compound A.

In Example 2, the solution was cooled in a reactor jacket to 70° C. immediately after reaching the maximum temperature of approximately 120-125° C. The cooling rate was about 1° C./minute, and the solution was held at 70° C. overnight to form over-acetylated Compound A before moving on to the next deacetylation process step to form Compound A.

Deacetylation: After acetylation, the reaction solution containing over-acetylated Compound A was concentrated under reduced pressure, before methanol and water was added prior to the deacetylation step. Sodium hydroxide was then added to methanol-water reaction mixture to carry out the deacetylation. The resulting reaction mixture was then further diluted with water before crystallization.

Crystallization: To achieve crystallization, hydrochloric acid was first added until the reaction mixture until it was slightly turbid, and then the reaction mixture was seeded with Compound A. The resulting slurry was stirred for 45 minutes before additional hydrochloric acid was added until about pH 7. The slurry was then cooled to 15° C. over night. Next day the slurry was filtered, and the filter cake was washed with methanol and then dried in a vacuum oven.

The reaction mixture was analysed by HPLC prior to the crystallization step, and the total level of by-products formed during the acetylation synthesis was 1.38% in Example 1, and 1.34% in Example 2. The majority of the by-products being formed during the acetylation step.

Both experiments resulted in a total concentration of Compound A and by-products in the mother liquor separated in the filtration step after the crystallization of 1.1 g/100 mL.

Comparative Examples 3 and 4 (Alternative Acetylation)

Acetylation: For each of Examples 3 and 4, Compound B (200 g) was added to a mixture of acetic anhydride (150.4 mL) and acetic acid (141.6 mL) to form a slurry. PTSA (1.6 g) was separately dissolved in a small amount of acetic anhydride (3.0 mL). The slurry was heated to approximately 60° C., before the PTSA solution was added over a period of approximately 2 hours to form over-acetylated Compound A, before moving on to the next deacetylation process step to form Compound A.

In Example 3, the temperature was held at 80-85° C. while PTSA solution was added, and kept at 80° C. overnight.

In Example 4, the temperature was held at 65-70° C. while PTSA was added, and kept at 65° C. overnight.

Deacetylation: After acetylation, the reaction mixture containing overacetylated Compound A was concentrated under reduced pressure, before methanol and water was added prior to the deacetylation step. Sodium hydroxide was then added to methanol-water reaction mixture to carry out the deacetylation. The resulting reaction mixture was then further diluted with water before crystallization.

Crystallization: To achieve crystallization, hydrochloric acid was first added until the reaction mixture until it was slightly turbid, and then the reaction mixture was seeded with Compound A. The resulting slurry was stirred for 45 minutes before additional hydrochloric acid was added until about pH 7. The slurry was then cooled to 15° C. over night. Next day the slurry was filtered, and the filter cake was washed with methanol and then dried in a vacuum oven.

The reaction mixture was analysed by HPLC prior to the crystallization step, and the total level of by-products formed during the acetylation synthesis was 0.11% in Example 3, and 0.10% in Example 4.

Both experiments resulted in a total concentration of Compound A and by-products in the mother liquor separated in the filtration step of 0.6 g/100 mL. The alternative acetylation gave an increased total purity of A by approximately 0.2% points after crystallization, compared to the established process, analysed by HPLC.

All patents, journal articles, publications and other documents discussed and/or cited above are hereby incorporated by reference.

We claim:

1. A process comprising the steps of:
   (i) reacting 5-amino-N,N'-bis(2,3-dihydroxypropyl)-2,4,6-triiodoisophthalamide ("Compound B") with a mixture of acetic anhydride/acetic acid to form a slurry;
   (ii) heating said slurry to about 60° C.; and
   (iii) adding an acid catalyst to said slurry at a rate such that the reaction temperature is maintained at a temperature range of about 65-85° C.

2. The process according to claim 1, further comprising the step of:
   (iv) adding a deacetylating agent to the reaction mixture of step (iii).

3. The process according to claim 2, further comprising the step of:
   (v) purifying the reaction mixture of step (iv).

4. The process according to claim 3, wherein said purifying step is a crystallization step.

5. The process according to claim 4, wherein said crystallization step achieved by seeding with 5-acetamido-N,N'-bis(2,3-dihydroxypropyl)-2,4,6-triiodoisophthalamide ("Compound A").

6. The process according to claim 5, wherein said acid catalyst is a sulfonic acid.

7. The process according to claim 6, wherein said acid catalyst is para-toluene sulfonic acid (PTSA).

8. The process according to claim 7, wherein said PTSA is added in a catalytic amount as a solid.

9. The process according to claim 7, wherein said PTSA is added in a catalytic amount as a solution of PTSA dissolved in a small volume of acetic anhydride.

* * * * *